United States Patent [19]

Mallipudi et al.

[11] Patent Number: 4,608,371

[45] Date of Patent: Aug. 26, 1986

[54] COMBATING INSECTS WITH CERTAIN 2,3-DIHYDRO-2,2-DIMETHYL-7-BENZOFURANYL N-OXALYL-N-METHYL CARBAMATES

[75] Inventors: Narayana M. Mallipudi, Lawrenceville, N.J.; John G. Hollingshaus, Yardley, Pa.

[73] Assignee: American Cyanamid Company, Stamford, Conn.

[21] Appl. No.: 710,796

[22] Filed: Mar. 11, 1985

[51] Int. Cl.[4] .................... A01N 47/22; C07D 307/86
[52] U.S. Cl. .................................... 514/186; 514/469; 549/212; 549/470

[58] Field of Search ................ 549/470, 212; 514/469, 514/186

[56] References Cited

U.S. PATENT DOCUMENTS 4,507,292  3/1985  Heywang et al. .................. 549/470
4,532,256  7/1985  Drabek .............................. 514/469

Primary Examiner—Henry R. Jiles
Assistant Examiner—Bernard I. Dentz
Attorney, Agent, or Firm—H. G. Jackson

[57] ABSTRACT

The present invention provides novel insecticidal carbamate derivatives. The invention also provides a method for the control of insects.

13 Claims, No Drawings

COMBATING INSECTS WITH CERTAIN 2,3-DIHYDRO-2,2-DIMETHYL-7-BENZOFURANYL N-OXALYL-N-METHYL CARBAMATES

BACKGROUND OF THE INVENTION

The derivatization of known insecticide compounds to produce novel compounds which exhibit improved properties such as greater residual effectiveness, lower mammalian toxicities and still retain their insecticidal activity continues to provide new and useful insecticides. Efforts with carbamate insecticides in particular have yielded a variety of new insecticidal compounds such as those described in DE 3,205,195, European Patent application EP-113-317-A, and those described in J. Agr. Food Chem. Vol. 21, No. 5 (1973) and Vol. 26, No 3 (1978) by T. R. Fukuto, et al. The continuing effort and promising results obtained in this area of research has renewed interest in the potential for a new generation of improved carbamate insecticides.

The present invention is novel insecticidal carbamate derivatives of formula I

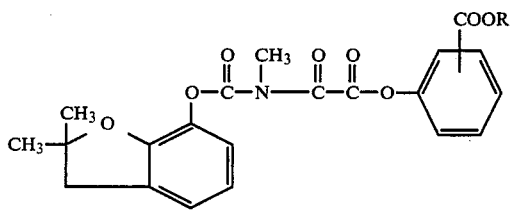

wherein R is H, $C_1$–$C_4$ lower alkyl, benzyl and salts of the acid. The novel carbamates of formula I in which the COOR group is in the o, m, and p, position and represents a carboxylic acid function, a carboxylate salt function, and a carboxylic ester function have been found to be highly effective insecticides, which possess systemic insecticidal activity and exhibit greatly reduced mammalian toxicity compared to carbofuran, the carbamate insecticide from which they are derived.

Preferred formula I compounds are those in which R is H, $C_1$–$C_4$ alkyl, and salts of the acid wherein R is a salt-forming cation such as a cation of alkali metals, such as sodium, potassium; alkaline earth metals; manganese, copper, iron, zinc, cobalt, lead, silver, nickel, ammonium or organic ammonium wherein preferred organic ammonium salts are defined as a group consisting of a positively charged nitrogen atom joined to from one to four aliphatic groups each containing one to 20 carbon atoms. Among the organic ammonium groups which are illustrative for the preparation of the aliphatic ammonium salts of the formula (I) benzoic acids herein are: monoalkylammonium, dialkylammonium, trialkylammonium, tetraalkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, $C_5$–$C_6$-cycloalkylammonium, piperidinium, morpholinium, pyrrolidinium, benzylammonium and equivalents thereof.

The compounds of the invention may readily be prepared by the reaction of carbofuran with oxalyl chloride in a temperature range of 0° C. to 150° C. and preferably 60° C. to 120° C. in an inert organic solvent such as ethers (diethyl ether, dioxane or tetrahydrofuran), hydrocarbons (such as benzene, toluene or xylene), chlorinated hydrocarbons (such as chloroform, dichloroethane or chlorobenzenes), and nitriles, ketones and esters, and mixtures of these solvents.

The hydrogen chloride formed in the reaction can be flushed out with gases, such as air or nitrogen, or escapes owing to the reaction temperature. Sodium carbonate, sodium bicarbonate or a tertiary organic base, such as triethylamine, benzyldimethylamine or N-N-dimethylaniline, may be added to the mixture to neutralize the acid.

The thus-formed product may then be reacted with an o, m or p-hydroxybenzoic acid ester in an inert organic solvent as described above in the presence of a base as described above to yield the desired formula I compound as illustrated in Flow Diagram (I) below.

Formula I compounds wherein R is H may then be prepared from the esters by hydrogenation of the thus-formed esters.

If a salt of the benzoic acid is desired, the thus-formed formula I compound wherein R is H may be reacted with the appropriate base in suitable solvent such as water, an alcohol, ether, hydrocarbon or chlorinated hydrocarbon solvent. If the isolation of the salt is desired, the reaction is preferably conducted in an organic solvent which may be removed by distillation under reduced pressure.

FLOW DIAGRAM I

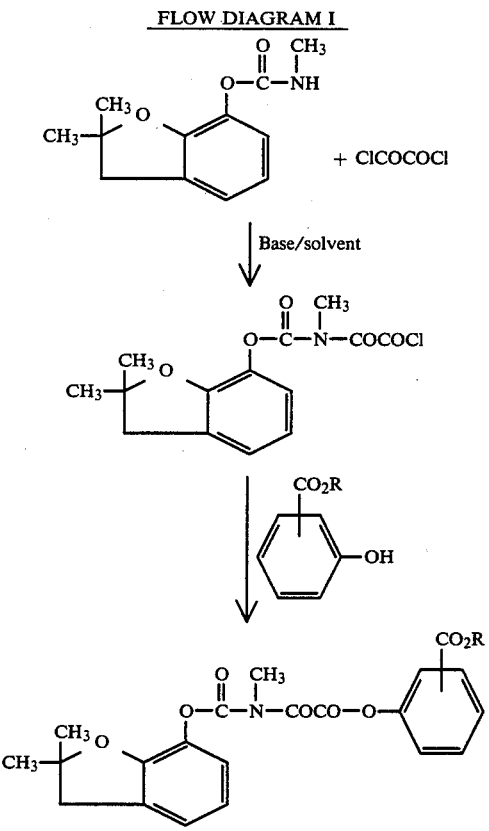

wherein R is $C_1$–$C_4$ alkyl, or benzyl.

The novel formula I compounds of the invention are exceedingly effective for the control of a wide variety of insect pests.

For the control of insects, including soil insects, which attack growing plants and/or harvested crops, including stored grain, the insecticidal compounds of this invention may be applied to the foliage of plants, or onto the soil in which the plants are grown, the insects' habitat and/or the insects' food supply. The active compound may be applied in the form of a dilute liquid spray; however, it may also be formulated as an emulsifiable concentrate, flowable concentrate, aerosol, dust, wettable powder, granules or the like.

These formulations may be produced by known procedures, by mixing the active formula (I) compound with inert liquid or solid diluents and carriers, optionally containing surface-active agents such as surfactants, wetting agents, dispersing agents and the like.

Some examples of liquid diluents, carriers, and solvents, that are suitable include, aromatic hydrocarbons, such as xylene, toluene or alkyl naphthalenes, chlorinated aromatic or chlorinated aliphatic hydrocarbons, such as chlorobenzenes, chlorethylenes or methylene chloride, aliphatic or alicyclic hydrocarbons, such as cyclohexane or paraffins, mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, and water.

Solid carriers that may be used include ground natural minerals, such as kaolins, clays, talc, chalk, quartz, attapulgite, montmorillonite or diatomaceous earth, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic material such as sawdust, coconut shells, maize cobs, tobacco stalks and the like.

Suitable surface active agents include nonionic and anionic surfactants, such as polyoxyethylene-fatty acid esters, polyoxyethylene-fatty alcohol ethers, for example alkylaryl polyglycol ethers, alkyl sulfonates, alkyl sulfates, aryl sulfonates lignin sulfonates and the like.

Formulations in general contain from 0.1% to 95% by weight and preferably 2% to 50% by weight of the active formula I compound.

The invention is further illustrated by the examples below, which are presented as illustrative and are not to be considered as limitative.

EXAMPLE 1

Preparation of N-(2,3-dihydro-2,2-dimethyl-7-benzofuranyl)carboxymethyloxamate, ester with methyl salicylate Oxalyl chloride (1.5 g, 0.012 mol) is added dropwise to a stirred solution of carbofuran (2.2 g, 0.01 mol) in 30 mL of 1,2-dichloroethane. Upon completion of the addition the reaction mixture is warmed slowly to 80° C. and maintained at this temperature until no more gas is evolved. The reaction mixture is cooled to room temperature and the solvent removed by distillation under reduced pressure to yield a viscous oil. The oil is dissolved in anhydrous diethylether (20 mL) and methyl salicylate (1.5 g, 0.010 mol) is added dropwise to the stirred solution followed by the dropwise addition of triethylamine (1.5 g, 0.015 mol). Upon completion of the addition the reaction mixture is allowed to stir at room temperature for three hours, filtered, and the organic filtrate washed with water. The organic phase is separated, dried over anhydrous magnesium sulfate, filtered, and the solvent removed under reduced pressure.

The oily residue is treated with an ether-hexane mixture and the resulting white solid filtered off and dried to give N-(2,3-dihydro-2,2-dimethyl-7-benzofuranyl)-carboxymethyloxamate, ester with methyl salicylate (compound number 2) with mp 106° C. to 108° C.

Utilizing the above procedure and substituting the appropriate ortho, meta or para hydroxybenzoate ester for methyl salicylate the N-(2,3-dihydro-2,2-dimethyl-7-benzofuranyl)carboxymethyloxamate benzoate esters listed in Table I below are prepared.

TABLE I

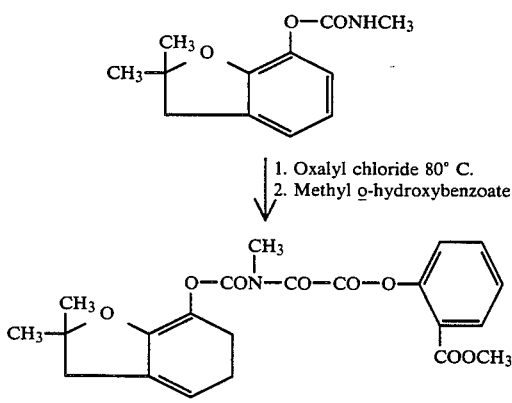

| Compound | Positional isomer | R | mp °C. |
|---|---|---|---|
| 1 | 4 | CH$_3$ | 146–148 |
| 2 | 2 | CH$_3$ | 106–108 |
| 3 | 3 | CH$_3$ | oil |
| 4 | 4 | n-C$_4$H$_9$ | 86–90 |
| 5 | 2 | C$_2$H$_5$ | low melting point |
| 6 | 2 | CH$_2$—C$_6$H$_5$ | 132–135 |
| 7 | 4 | CH$_2$—C$_6$H$_5$ | 84–85 |

EXAMPLE 2

Preparation of N-(2,3-dihydro-2,2-dimethyl-7-benzofuranyl)carboxymethyloxamate, ester with p-hydroxybenzoic acid

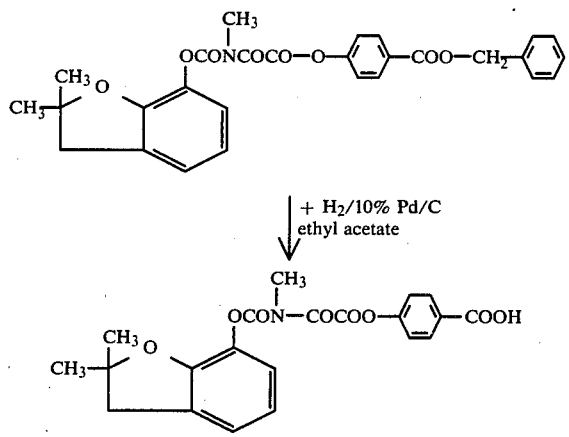

The benzyl ester of p-hydroxybenzoic acid ester with N-(2,3-dihydro-2,2-dimethyl-7-benzofuranyl)carboxymethyloxamate (1.5 g) dissolved in 20 mL of ethyl acetate is added to 20 mL of ethyl acetate containing a catalytic amount (330 mg) of 10% palladium on carbon. The resulting mixture is stirred and hydrogen gas (120 mL) introduced over a 2.5 hour period at room temperature. Upon completion of the hydrogen addition, the reaction mixture is filtered to remove solids and the organic filtrate concentrated under reduced pressure to yield 1.93 g (93% yield) of the title product with mp 165° to 166° C., compound number 8.

In a similar manner, the formula (I) compounds listed below may be prepared.

TABLE II

| Compound | Positional isomer | mp °C. |
|---|---|---|
| 9 | 3 | 165–170 |
| 10 | 2 | — |

EXAMPLE 3

Preparation of Salts

An acetone solution containing about 1 molar equivalent of an amine or quaternary ammonium hydroxide is added to an acetone solution containing the appropriate benzoic acid isomer, the mixture is stirred until salt formation is complete. A portion of the resulting solution is evaporated to dryness and the residue identified by its infrared spectral properties.

Utilizing this procedure yields the formula (I) compounds listed in Table III below.

TABLE III

| Compound | Positional isomer | R |
|---|---|---|
| 11 | 4 | isopropylammonium |
| 12 | 4 | dipolyethoxylated octadecylammonium |
| 13 | 4 | benzyltrimethylammonium |
| 14 | 4 | triethylammonium |
| 15 | 4 | 4-phenylbutylammonium |
| 16 | 4 | dicyclohexylammonium |
| 17 | 3 | isopropylammonium |
| 18 | 3 | dipolyethoxylated octadecylammonium |
| 19 | 3 | benzyltrimethylammonium |
| 20 | 3 | triethylammonium |
| 21 | 3 | 4-phenylbutylammonium |
| 22 | 3 | dicyclohexylammonium |

EXAMPLE 4

Insecticidal activity of the compounds of the invention

The insecticidal activity of the compounds of the present invention against a variety of insects at various concentrations of active ingredient in acetone-water solutions is determined by the following insecticidal test examples. The results of these tests which are summarized in Table IV below demonstrate the effectiveness of compounds of formula (I) as insecticides.

*Heliothis virescens*, egg, tobacco budworm

A young cotton leaf about 7–8 cm long is dipped in a test suspension with agitation for three seconds. Eggs are collected on cheesecloth and cut into 10–20 mm squares containing about 50–100 eggs (6–30 hours old). A square of cheesecloth with eggs is also dipped similarly in the test suspension and placed on the treated leaf. The combination is placed in the hood to dry. Following this, the combination is placed in an 8 ounce Dixie Cup #2168-ST (240 mL, 6 cm tall, top diameter 9.5 cm, bottom diameter 8 cm), containing a 5 cm length of damp dental wick. A clear plastic lid is put on the top of the cup and the treatments held for three days before mortality counts are made.

*Aphis fabae*, mixed instars, bean aphid

Pots containing single nasturtium plants (Tropaeolum sp) about 5 cm tall are infested with about 100–200 aphids one day before the test. Each pot is sprayed with the test formulation for two revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for two days, following which mortality estimates are made.

*Spodoptera eridania*, third-instar larvae, southern armyworm

The leaves of a Sieva lima bean plant expanded to 7–8 cm in length are dipped in a test suspension with agitation for three seconds and placed in a hood to dry. A leaf is then excised and placed in a 100×10 mm petri dish containing a damp filter paper on the bottom and ten third-instar larvae. The dish is maintained for five days before observations are made of mortality, reduced feeding, or any interference with normal moulting.

*Spodoptera eridania*, seven-day residual

The plants treated in the above test are maintained under high intensity lamps in the greenhouse for seven days. These lamps duplicate the effects of a bright sunny day in June in New Jersey and are kept on for a 14 hour day length. After seven days, the foliage is sampled and assayed as above.

*Tetranychus urticae* (P-resistant strain), two-spotted spider mite

Sieva lima bean plants with primary leaves expanded to 7–8 cm are selected and cut back to one plant per pot. A small piece is cut from a leaf taken from the main mite colony and placed on each leaf of the test plants. This is done about two hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for three seconds with agitation and set in the hood to dry. Plants are kept for two days before estimates of adult kill are made using the first leaf. The second left is kept on the plant for another five days before observations are made of the kill of eggs and/or newly emerged nymphs.

*Diabrotica undecimpunctata howardi*, Third-instar southern corn rootworm

One cc of fine talc is placed in a 30 mL wide-mouth screw-top glass jar. One mL of the appropriate acetone suspension is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer ®. Following this, ten third-instar rootworms are added to each jar and the jars loosely capped to allow air exchange for the larvae. The treatments are held for 6 days before mortality counts are made. Missing larvae are presumed dead, since they decomposed rapidly and cannot be found. The concentrations used in this test correspond approximately to 50 and 10 kg/ha, respectively.

*Anopheles quadrimaculatus*, eggs and first-instar, common malaria mosquito

Concentrations of 1.2 and 0.4 ppm are obtained by pippetting 1 mL of 300 and 100 ppm acetone solutions or suspensions of the compound into a 400 mL beaker containing 250 mL of deionized water. The contents are stirred with the pipette as the 1 mL is added. A wax paper ring about 1 cm wide is floated on the surface of the water to keep the eggs from floating up the meniscus curve and drying out on the side of the beaker. A spoon made from screen is used to transfer about 100 eggs (6–30 hours old) into the test beaker. The beakers are held for two days, following which observations of kill of eggs, kill of newly emerged larvae or delayed hatch are recorded.

*Anopheles quadrimaculatus*, adults, common malaria mosquito

Acetone test suspensions are poured into 60 mL wide-mouth jars each containing a microscope slide. The slides are removed from the test suspensions with clean forceps and placed to dry horizontally on the mouths of 120 mL wide-mouth jars. When dry, they are put into the same 120 mL jars. Ten four-to-five day old adult mosquitoes of mixed sexes are placed in each jar with the treated microscope slide. A piece of cheesecloth held on by an elastic band serves as a lid for the jar. A wad of cotton soaked in 10% honey solution is placed on the lid as a food supply for the mosquitoes. Treatments are held for one day before mortality counts are made.

*Lygus lineolaris*, adults, tarnished plant bug

About 5 cm long primary leaves of Sieva lima beans are dipped in the test formulation for three seconds with agitation and placed in the hood to dry. The leaf is then placed in an 8 ounce Dixie Cup #2168-ST (240 mL, 6 cm high, 9.5 cm top diameter, 8 cm bottom diameter) into which a 5 cm length of damp dental wick has been previously placed. Insects are aspirated out of the colony and ten insects placed in each cup. Treatments are held for three days, following which mortality counts are made.

*Empoasca abrupta*, adults, western potato leafhopper

A Sieva lima bean leaf about 5 cm long is dipped in the test formulation for three seconds with agitation and placed in a hood to dry. The leaf is placed in a 100×10 mm petri dish containing a moist filter paper on the bottom. About ten adult leafhoppers are added to each dish and the treatments are kept for three days before mortality counts are made.

*Heliothis virescens*, third-instar tobacco budworm

Cotton cotyledons are dipped in the test formulation and allowed to dry in a hood. When dry, each is cut into quarters and ten sections placed individually in 30 mL plastic medicine cups containing a 5–7 mm long piece of damp dental wick. One third-instar caterpillar is added to each cup and a cardboard lid placed on the cup. Treatments are maintained for three days before mortality counts and estimates of reduction in feeding damage are made.

Southern armyworm (*Spodoptera eridania*), third-instar, cut-stem systemic test

The compound is formulated as an emulsion containing 0.1 gm of the test material, 0.1 gm of a polyoxyethylated vegetable oil in 0.4 g water, 10 mL of acetone and 90 mL of water. This is diluted ten-fold with water to give the 100 ppm emulsion for the test. Subsequent ten-fold dilutions are made with water as needed, to provide 10 ppm and 1 ppm test emulsions. Sieva lima bean plants with just the primary leaves expanded are used in this test. They are cut off at least 2.5 cm above the soil level to avoid contamination with soil bacteria that will cause decay of the stem during the test.

Sixty mL bottles containing 50 mL of the test emulsion at 100 ppm initially each have one Sieva lima bean stem inserted into the emulsion. The stem is wrapped with a bit of cotton to hold the end off the bottom of the bottle and to limit evaporation. The test bottles are held for three days at 27° C. to enable the compound to be taken up into the leaf, keeping the room fluorescent lights on for 24 hours/day. Following this, one leaf is removed from the plant and placed in a 100×10 mm petri dish with ten southern armyworms. The petri dishes are held for three days at 27° C. before mortality counts and notations of feeding damage are taken.

Two-spotted spider mite (*Tetranychus urticae*), adult, susceptible strain, cut-stem systemic test Sixty mL bottles containing 50 mL of the test emulsion at 100 ppm each have one cut Sieva lima bean inserted in the emulsion. The stem is wrapped with a bit of cotton to hold the stem off the bottom and to limit evaporation and volatilization of the compound. The bottle is then placed in a ventilated box with the leaves extending outside the box, such that any possible fumes from the compound will be drawn out of the end of the box rather than rising to affect the test leaves. About 50 adult mites are placed on each leaf. Tests are held for three days at 27° C. before mortality estimates are made using a 10× microscope.

*Blattella germanica*, bait test, adult male German Cockroach

A 0.1% bait is prepared by pipetting 1 mL of a 1000 ppm solution of the test compound in acetone onto 1 gm of cornmeal in a 30 mL wide-mouth bottle. The bait is dried by passing a gentle stream of air into the bottle. The bait is placed in a one pint wide-mouth Mason jar and ten adult male cockroaches are added. A screen lid is placed on the jar and a small piece of cotton soaked in 10% honey is put on the top of the screen lid. Mortality counts are made after three days.

*Blattella germanica*, residue test, adult male German cockroach

One mL of a 1000 ppm acetone solution of the test material is pipetted slowly over the bottom of a 150×15 mm petri dish so as to give as uniform coverage as possible. After the deposit has dried, ten adult male cockroaches are placed in each dish and the lid is added. Mortality counts are made after three days.

The rating system employed in these tests is as follows:

| Rating System |
| --- |
| 0 = 0–10% kill |
| 1 = 10–25% kill |
| 2 = 26–35% kill |
| 3 = 36–45% kill |
| 4 = 46–55% kill |
| 5 = 56–65% kill |
| 6 = 66–75% kill |
| 7 = 76–85% kill |
| 8 = 86–99% kill |
| 9 = 100% kill |

The absence of a number indicates that no test has been run at that particular dosage.

Data obtained are reported in Table IV below.

TABLE IV

Summary of insecticidal activity

| Cpd No | Budworm eggs ppm 1000 | 100 | 10 | Bean aphids ppm 100 | 10 | 1 | Southern armyworms ppm 1000 | 100 | 10 | 7 days | SCRW kg/ha 50 | 10 | 1 | Malaria mosquito Larvae ppm 1.2 | .4 | .04 | .004 | Mosq. adult ppm 10 | 1 | Lygus ppm 100 | 10 | Leafhopper ppm 100 | 10 | 1 | TBW ppm 1000 | 100 | 10 | Systemic SAW ppm 100 | 10 | 1 | G. Cockroach residual ppm 1000 | 100 | 10 |
|---|---|---|---|---|---|---|---|---|---|---|---|---|---|---|---|---|---|---|---|---|---|---|---|---|---|---|---|---|---|---|---|---|---|
| 1 | 9 | 8 | 0 | 9 | 7 | 0 | 9 | 9 | 0 | 9 | 9 | 7 | 0 | 8 | 8 | 0 | — | 9 | 0 | 9 | 0 | 9 | 9 | 0 | 9 | 0 | — | 9 | 7 | — | 0 | — | — |
| 2 | 9 | 9 | 8 | 9 | 7 | 7 | 9 | 9 | 0 | 9 | 9 | 9 | 9 | 8 | 8 | 0 | — | 9 | 0 | 9 | 0 | 9 | 9 | — | 9 | 0 | — | 9 | 8 | 3 | 0 | — | — |
| 3 | 9 | 9 | 3 | 9 | 9 | 4 | 9 | 9 | 0 | 9 | 9 | 9 | 8 | 9 | 9 | 0 | — | 9 | 3 | 9 | 5 | 9 | 6 | — | 9 | 0 | — | 9 | 0 | — | 0 | — | — |
| 4 | 9 | 9 | 8 | 7 | 0 | 0 | 9 | 9 | 0 | 9 | 9 | 9 | 9 | 8 | 5 | 0 | — | 9 | 0 | — | — | 9 | 0 | — | 9 | 0 | 0 | 9 | 0 | 0 | 0 | 0 | — |
| 5 | 9 | 9 | 8 | 7 | 0 | 0 | 9 | 9 | 0 | 9 | 9 | 9 | 7 | 8 | 8 | 0 | — | 9 | 0 | — | — | 9 | 0 | 0 | 9 | 0 | — | 9 | 8 | 0 | 0 | 0 | — |
| 6 | 0 | — | 0 | 3 | — | — | 9 | 6 | 0 | 9 | 9 | 9 | 0 | 9 | 9 | 4 | — | 9 | 9 | — | — | 9 | 9 | — | 0 | — | — | 7 | 0 | 0 | 0 | 0 | — |
| 7 | 9 | 9 | 8 | 9 | 7 | 7 | 9 | 9 | 0 | 6 | 9 | 9 | 5 | 9 | 9 | 0 | — | 9 | 0 | — | — | 9 | 0 | 0 | 7 | 0 | 0 | 3 | 0 | 0 | 0 | 0 | — |
| 8 | 9 | 9 | 8 | 9 | 8 | 7 | 9 | 9 | 0 | 6 | 9 | 9 | 6 | 9 | 9 | 6 | — | 9 | 6 | — | — | 9 | 5 | 0 | 9 | 4 | 0 | 9 | 9 | 3 | 2 | 0 | — |
| 9 | — | 8 | 0 | 9 | 8 | 0 | 9 | 9 | 0 | 0 | — | — | — | 9 | 9 | 0 | — | 9 | 9 | — | — | 9 | 3 | 0 | 8 | 0 | 0 | 9 | 0 | 0 | 0 | 0 | — |
| 11 | — | 9 | 5 | 9 | 9 | 0 | 8 | 8 | 0 | 0 | 9 | 9 | 9 | 9 | 6 | 0 | — | 9 | 5 | — | — | 9 | 9 | 0 | 6 | 0 | 0 | 9 | 0 | 0 | 0 | 0 | — |
| 12 | — | 9 | 5 | 9 | 9 | 7 | — | 9 | 5 | 0 | 9 | 9 | 9 | 9 | 7 | 0 | — | 9 | 9 | — | — | 9 | 9 | 8 | 8 | 0 | 0 | 9 | 0 | 0 | 9 | 8 | — |
| 13 | — | 9 | 3 | 9 | 8 | 0 | — | 9 | 0 | 0 | 9 | 9 | 9 | 9 | 7 | 0 | — | 9 | 3 | — | — | 9 | 9 | 0 | 7 | 0 | 0 | 9 | 0 | 0 | 9 | 0 | — |
| 14 | — | 9 | 6 | 9 | 9 | 0 | — | 9 | 0 | 0 | 9 | 9 | 9 | 9 | 8 | 0 | — | 9 | 4 | — | — | 9 | 8 | 8 | 9 | 0 | 0 | 9 | 0 | 0 | 9 | 2 | — |
| 15 | — | 9 | 5 | 9 | 9 | 0 | — | 9 | 0 | 0 | 9 | 9 | 9 | 9 | 7 | 0 | — | 9 | 9 | — | — | 9 | 9 | 3 | 6 | 0 | 0 | 9 | 0 | 0 | 9 | 0 | — |
| 16 | — | 5 | 0 | 9 | 9 | 3 | — | 9 | 0 | 0 | 9 | 9 | 9 | 9 | 7 | 0 | — | 9 | 8 | — | — | 9 | 9 | 2 | 5 | 0 | 0 | 9 | 0 | 0 | 8 | 4 | — |
| 17 | — | 6 | 0 | 9 | 8 | 6 | — | 9 | 0 | 0 | — | — | — | 9 | 8 | 0 | — | 9 | 7 | — | — | 9 | 8 | 0 | 7 | 0 | 0 | 9 | 0 | 0 | 9 | 0 | — |
| 18 | — | 8 | 4 | 9 | 9 | 0 | — | 6 | 0 | 0 | — | — | — | 9 | 9 | 0 | — | 9 | 9 | — | — | 9 | 7 | 0 | 7 | 0 | 0 | 9 | 0 | 0 | 9 | 0 | — |
| 19 | — | 7 | 0 | 9 | 9 | 0 | — | 9 | 0 | 0 | — | — | — | 9 | 9 | 0 | — | 9 | 7 | — | — | 9 | 9 | 0 | 9 | 0 | 0 | 9 | 0 | 0 | 9 | 0 | — |
| 20 | — | 7 | 4 | 9 | 9 | 3 | — | 6 | 0 | 0 | — | — | — | 9 | 7 | 0 | — | 9 | 9 | — | — | 9 | 9 | 3 | 6 | 0 | 0 | 9 | 0 | 0 | 9 | 0 | — |
| 21 | — | 8 | 3 | 9 | 8 | 0 | — | 9 | 0 | 0 | — | — | — | 9 | 8 | 0 | — | 9 | 9 | — | — | 9 | 9 | 0 | 9 | 0 | 0 | 9 | 0 | 0 | 9 | 0 | — |
| 22 | — | 9 | — | 9 | 8 | 0 | — | 9 | 0 | 0 | — | — | — | 9 | 8 | 0 | — | 9 | 7 | — | — | 9 | 9 | 0 | 9 | 0 | 0 | 9 | 0 | 0 | 9 | 6 | — |

What is claimed is:
1. A compound having the formula

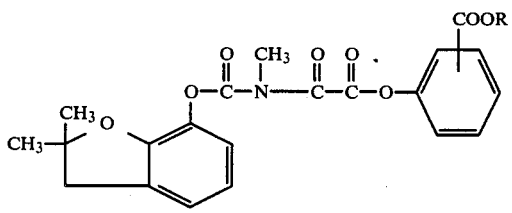

wherein R is H; $C_1$-$C_4$ lower alkyl, benzyl and salts of the free acid.

2. A compound according to claim 1 wherein R is a salt-forming cation of alkali metals, alkaline earth metals, manganese, copper, iron, zinc, cobalt, lead, silver, nickel, ammonium or organic ammonium.

3. A compound according to claim 1 having the structure:

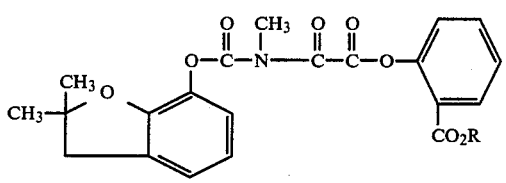

wherein R is H, $CH_3$ or $C_2H_5$.

4. The compound according to claim 3 wherein R is $CH_3$.

5. A compound according to claim 1 having the structure

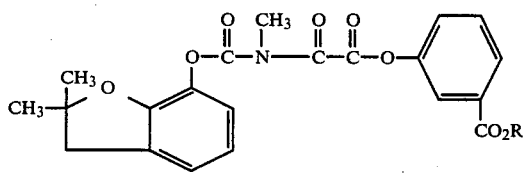

wherein R is H, $CH_3$ or $C_2H_5$.

6. The compound according to claim 5 wherein R is $CH_3$.

7. A compound according to claim 1 having the structure

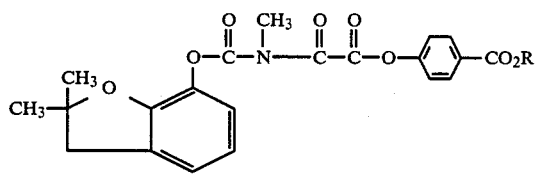

wherein R is H, $CH_3$ or $C_2H_5$.

8. The compound according to claim 7 wherein R is $CH_3$.

9. A method for controlling insects comprising applying to the insects, their habitat or food supply an insecticidally effective amount of a compound having the formula

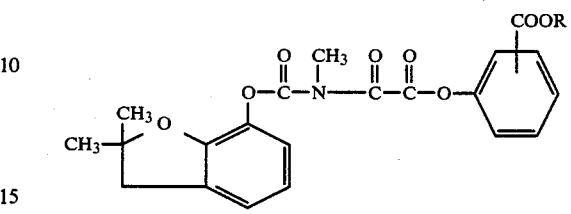

wherein R is H; $C_1$-$C_4$ lower alkyl, benzyl and salts of the free acid.

10. A method according to claim 9 comprising applying a compound, wherein R is a salt-forming cation of alkali metals, alkaline earth metals, manganese, copper, iron, zinc, cobalt, lead, silver, nickel, ammonium or organic ammonium.

11. A method according to claim 9 comprising applying a compound having the structure

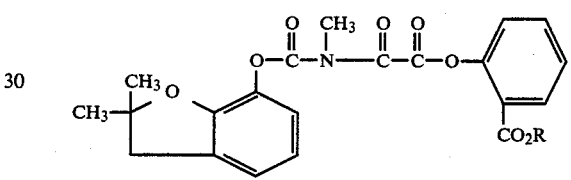

wherein R is H, $CH_3$ or $C_2H_5$.

12. A method according to claim 9 comprising applying a compound having the structure

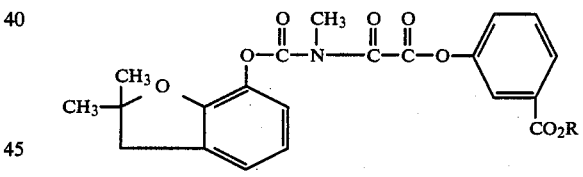

wherein R is H, $CH_3$ or $C_2H_5$.

13. A method according to claim 9 comprising applying a compound having the structure

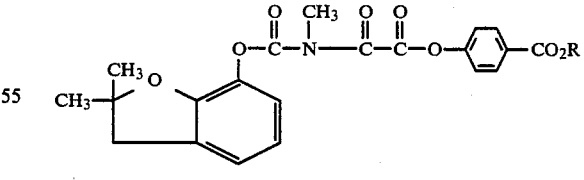

wherein R is H, $CH_3$ or $C_2H_5$.

* * * * *